(12) United States Patent
Yamanaka

(10) Patent No.: US 8,200,443 B2
(45) Date of Patent: Jun. 12, 2012

(54) ADJUSTMENT DEVICE OF ROTARY MACHINE, ADJUSTMENT METHOD OF ROTARY MACHINE, AND MANUFACTURING METHOD OF ROTARY MACHINE

(75) Inventor: Takeshi Yamanaka, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 751 days.

(21) Appl. No.: 12/346,160

(22) Filed: Dec. 30, 2008

(65) Prior Publication Data

US 2009/0177419 A1 Jul. 9, 2009

(30) Foreign Application Priority Data

Jan. 8, 2008 (JP) ................................. 2008-001427

(51) Int. Cl.
*G01F 17/00* (2006.01)
(52) U.S. Cl. ......................................................... 702/56
(58) Field of Classification Search .................... 702/56; 700/279; 416/144
See application file for complete search history.

(56) References Cited

U.S. PATENT DOCUMENTS

| 6,879,882 | B2* | 4/2005 | Montanari et al. ............ 700/279 |
| 2008/0003107 | A1* | 1/2008 | Carvalho ...................... 416/144 |

FOREIGN PATENT DOCUMENTS

| CN | 1371662 A | 10/2002 |
| JP | 5-70506 | 3/1993 |
| JP | 8-214512 | 8/1996 |
| JP | 2001-170038 | 6/2001 |
| JP | 2002-315745 | 10/2002 |
| JP | 2004-65477 | 3/2004 |
| JP | 2005-40604 | 2/2005 |
| JP | 2005-211662 | 8/2005 |

* cited by examiner

*Primary Examiner* — Drew A Dunn
*Assistant Examiner* — Xiuquin Sun
(74) *Attorney, Agent, or Firm* — Oblon, Spivak, McClelland, Maier & Neustadt, L.L.P.

(57) ABSTRACT

An adjustment device of a rotary machine including a movable base formed rotatable around an axis, vibration sensors formed so that the sensors can measure amplitudes of longitudinal vibration and transverse vibration of the rotary machine, an adjustment weight to be arranged on the movable base, and a PC including a control section for calculating a position and weight of the adjustment weight, a storage section, and an amplifier are provided, an approximate expression is obtained by the PC from an amplitude measured by the vibration sensor, and a predetermined function, an optimum change amount x and position θ of the adjustment weight are calculated from the approximate expression, whereby the adjustment weight is arranged.

7 Claims, 12 Drawing Sheets

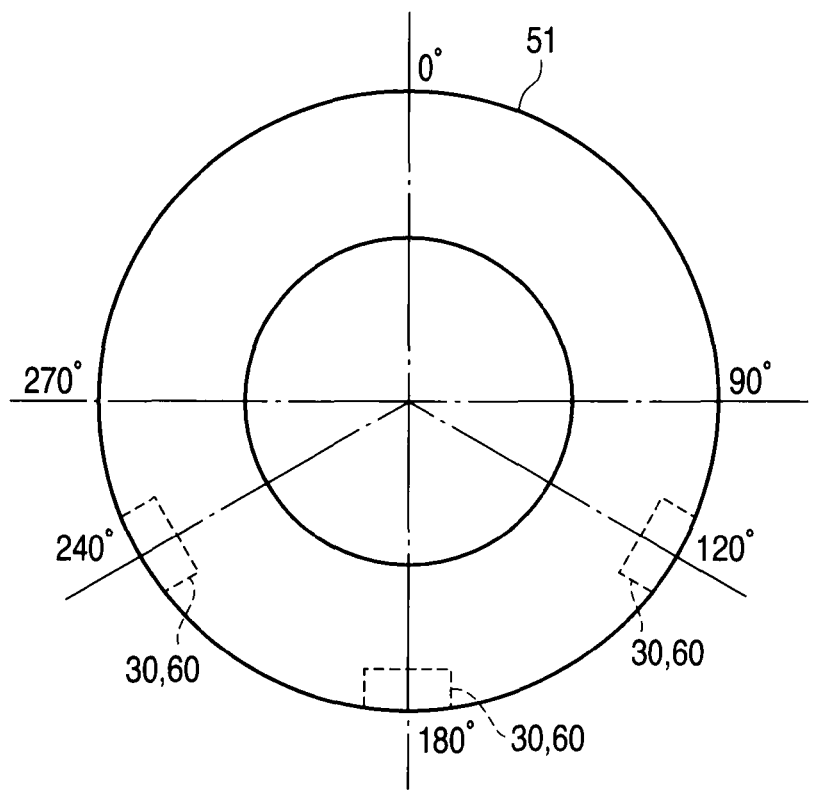
F I G. 3
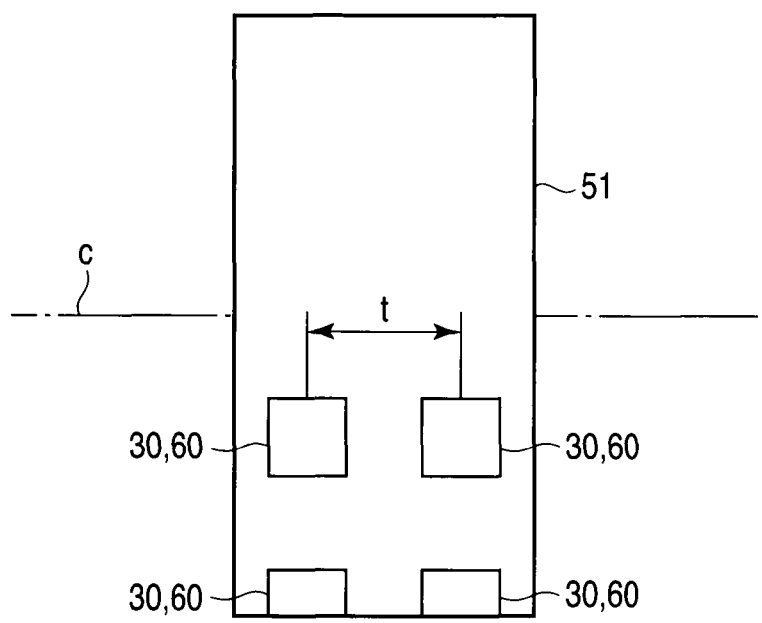
F I G. 4

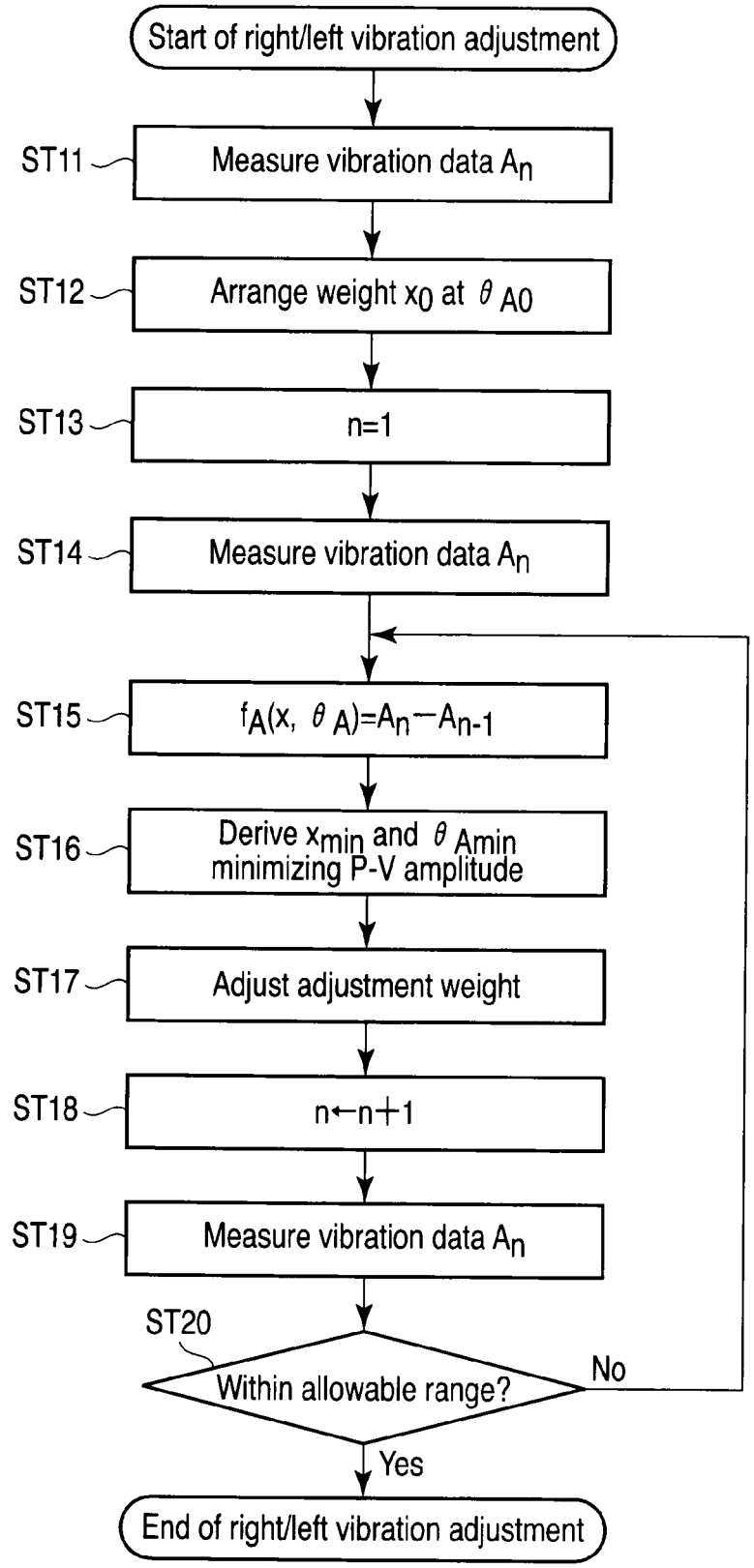
F I G. 5

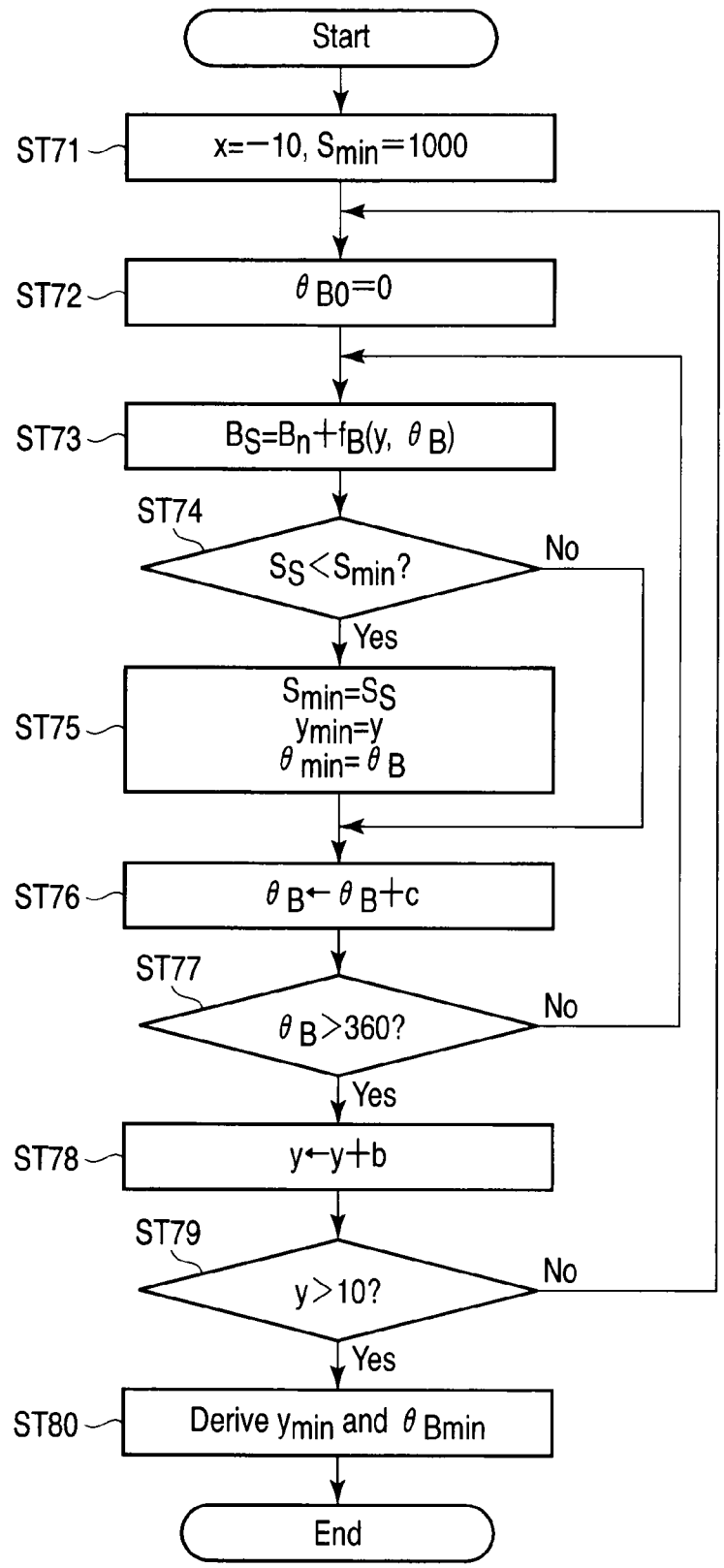
F I G. 8

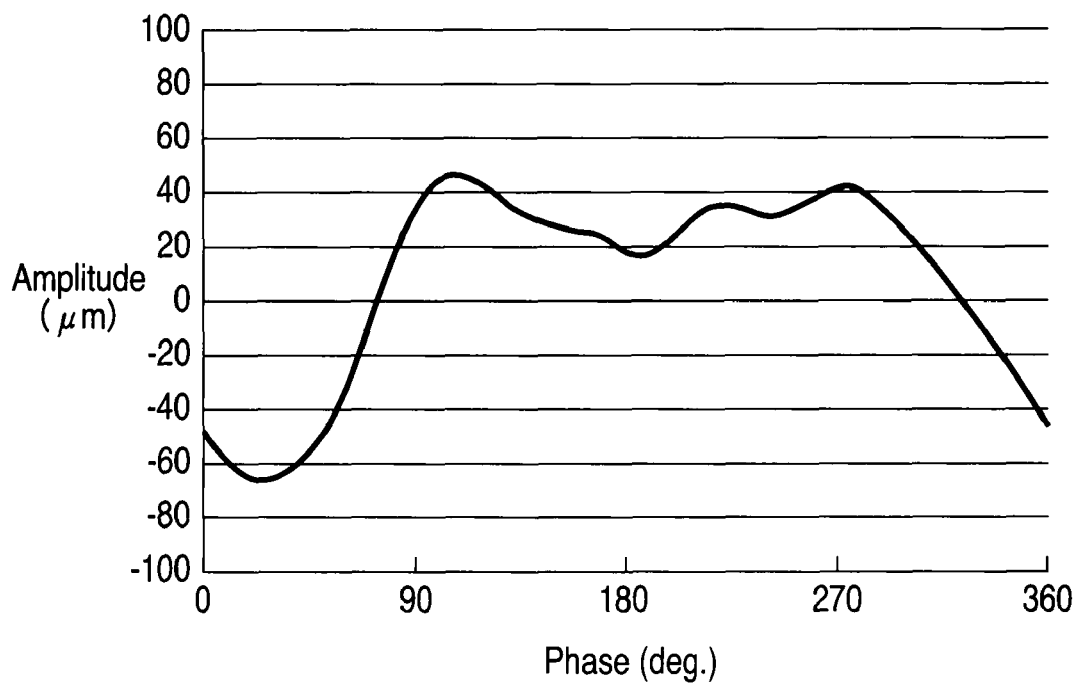
F I G. 9
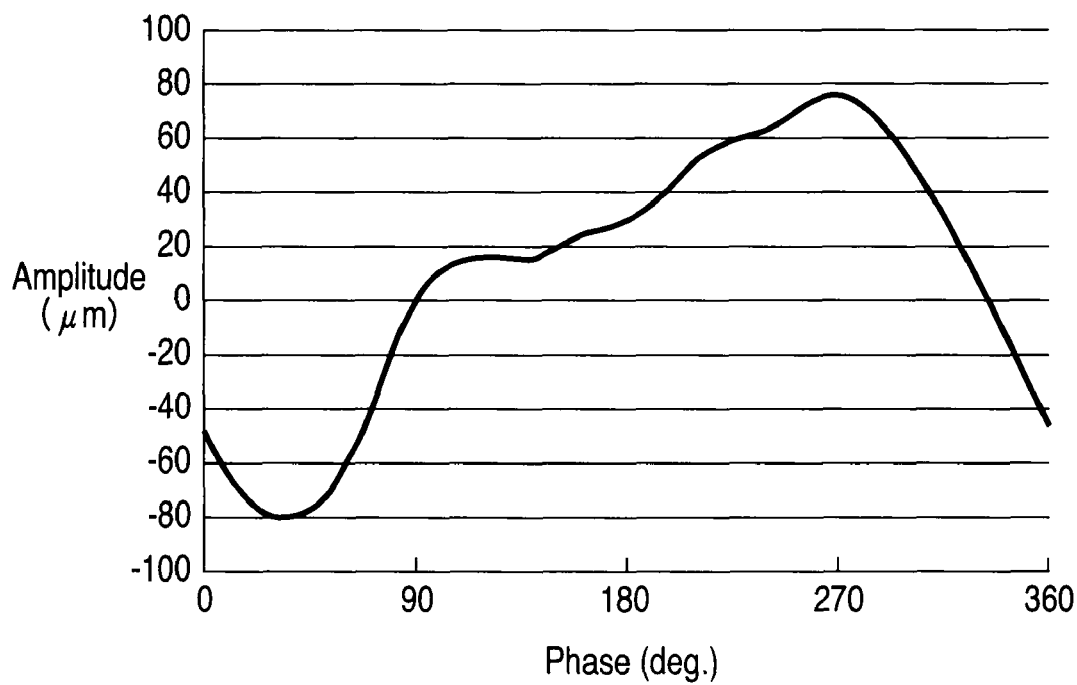
F I G. 10

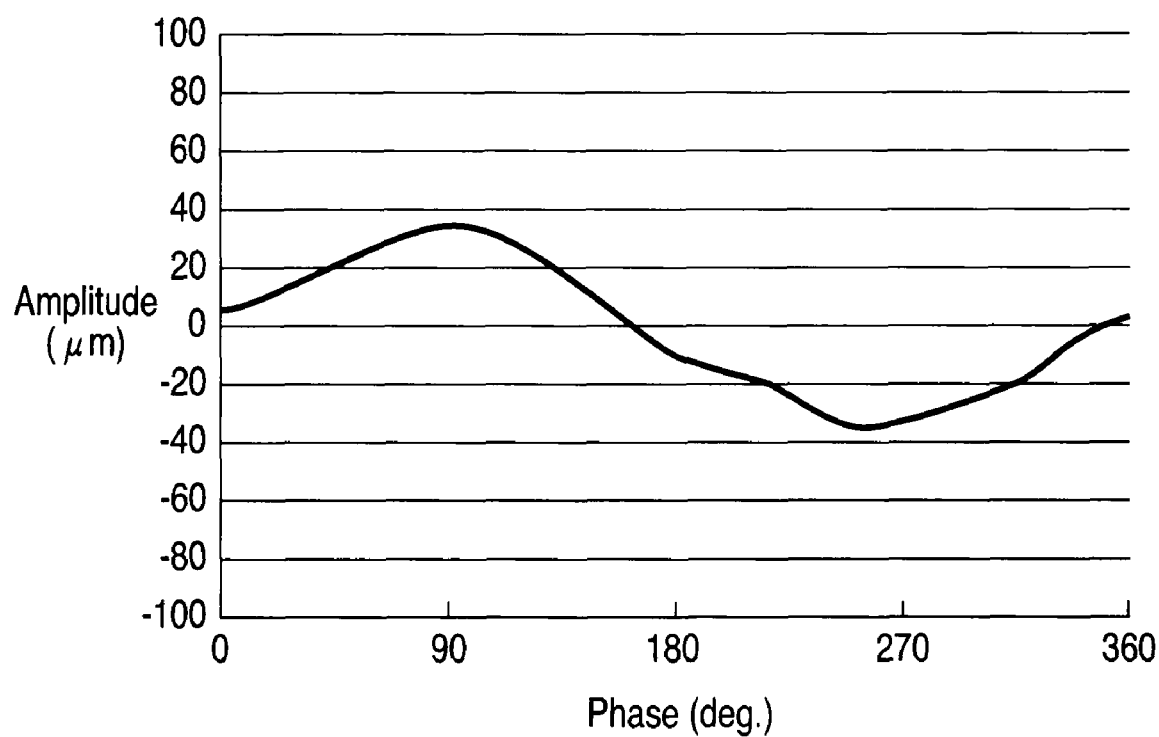
F I G. 11

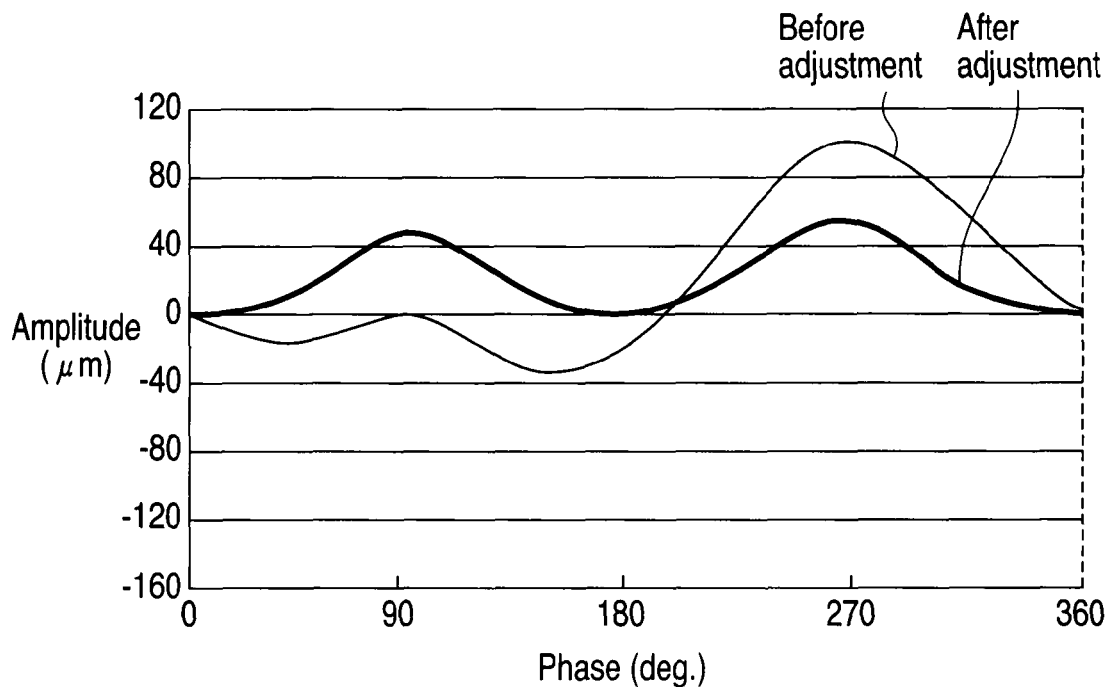
F I G. 12
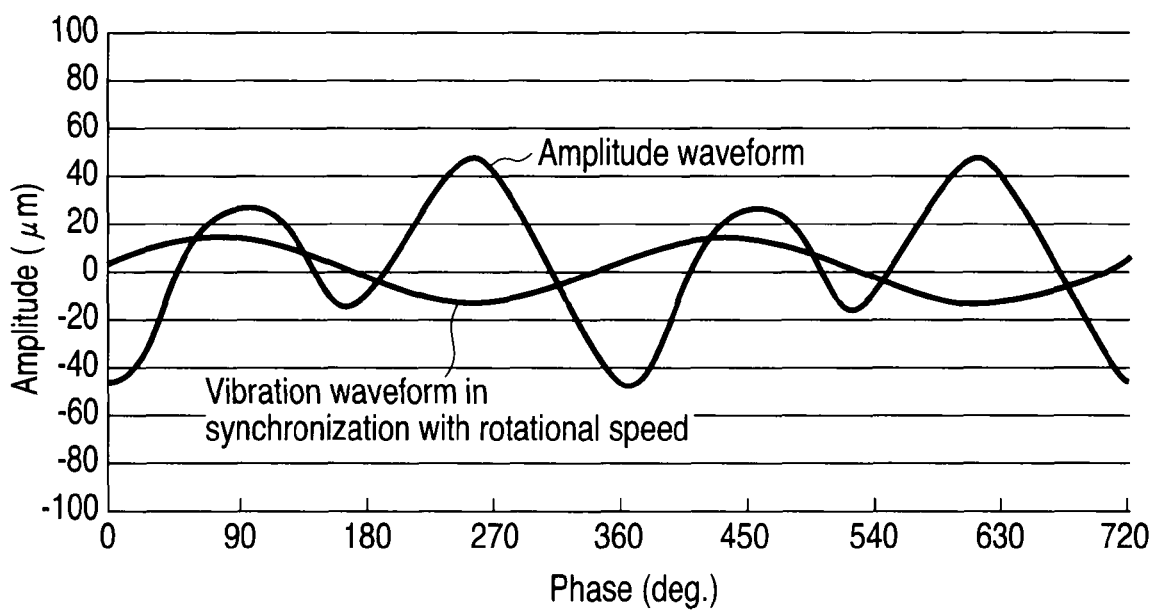
F I G. 13

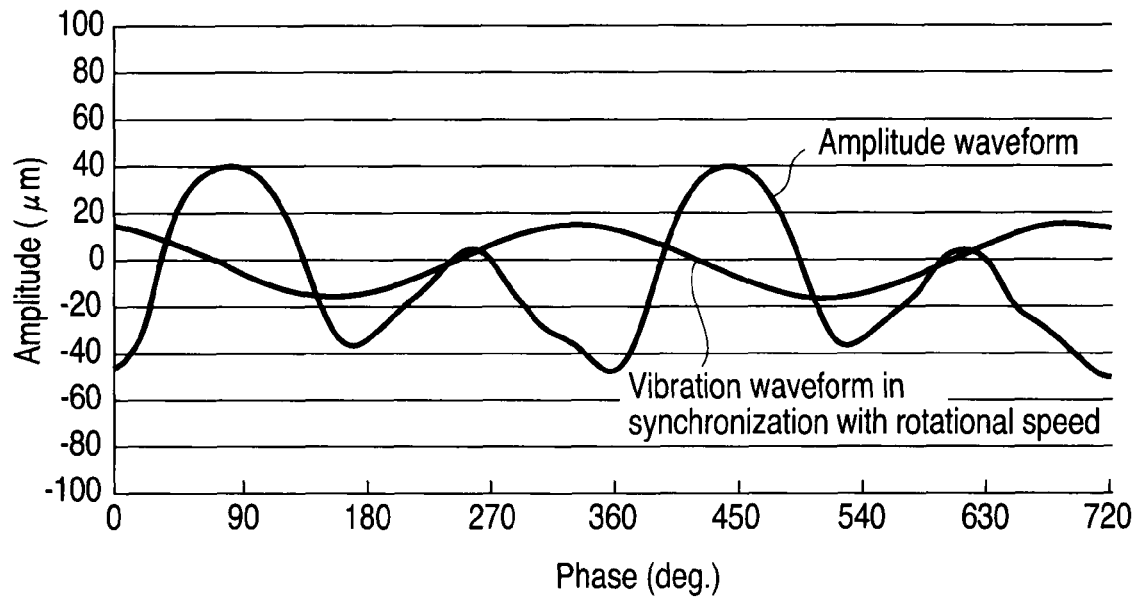
F I G. 14
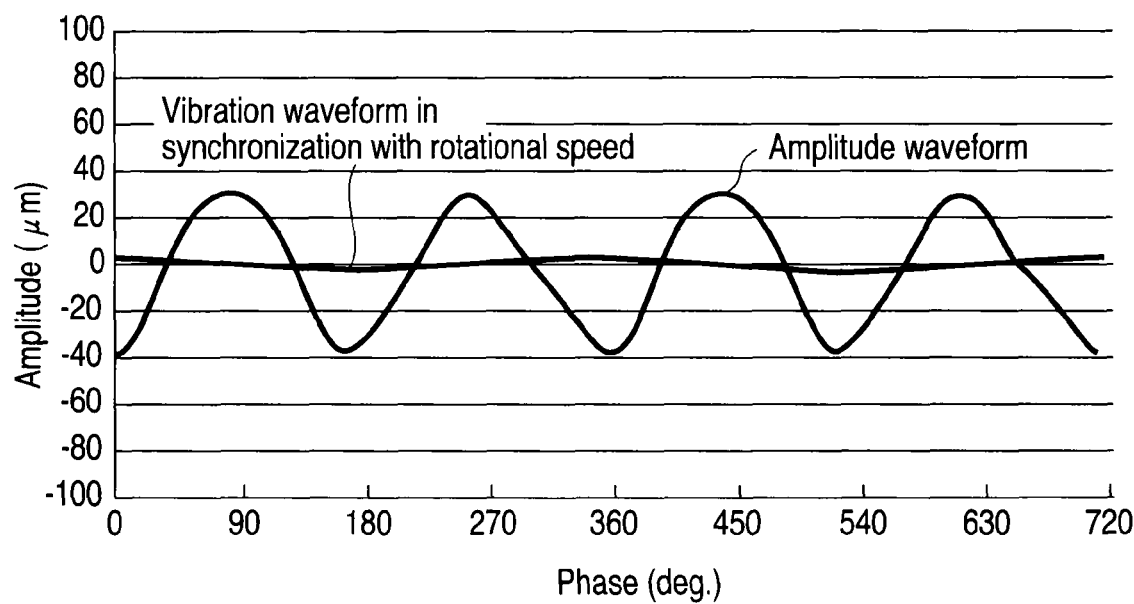
F I G. 15

ADJUSTMENT DEVICE OF ROTARY MACHINE, ADJUSTMENT METHOD OF ROTARY MACHINE, AND MANUFACTURING METHOD OF ROTARY MACHINE

CROSS-REFERENCE TO RELATED APPLICATIONS

This application is based upon and claims the benefit of priority from prior Japanese Patent Application No. 2008-001427, filed Jan. 8, 2008, the entire contents of which are incorporated herein by reference.

BACKGROUND OF THE INVENTION

1. Field of the Invention

The present invention relates to an adjustment device of a rotary machine for balance adjustment of a rotary machine at the time of rotation, an adjustment method of a rotary machine, and a manufacturing method of an X-ray CT apparatus, and more particularly, to an adjustment device, an adjustment method, and a manufacturing method by which balance adjustment at the time of rotation can be performed easily and with a high degree of accuracy.

2. Description of the Related Art

At present, in a medical site, an X-ray computed tomography (CT) apparatus is used in, for example, tomography using X-rays. The X-ray CT apparatus irradiates an subject with irradiation rays (X-rays) from every direction, observes projection data obtained by passing of the X-rays through the subject, and reproduces distribution of a desired physical quantity inside the subject from the projection data. Actually, a movable base including an X-ray tube and a detector is rotated around the subject (patient or the like) laid down on a bed, thereby performing tomography of the patient.

In a movable base used in such an X-ray CT apparatus, speed-enhancement of the movable base is contrived in order to improve the throughput or reduce the burden to the patient. Further, depending on the type of tomography, the movable base is rotated at a high speed, and there are even some cases where the tomographic plane is inclined toward the body axis at the time of rotation.

However, in the rotary machine such as the movable base and the like, the balance of rotation is not uniform at each position because of the configuration, weight, and the like. When such a rotary machine is rotated and inclined, rotation unbalance is caused. When the rotation unbalance occurs, vibration is produced in the rotary machine at the time of rotation. Particularly, the higher the rotation operation is, the larger the amplitude of the produced vibration is.

When vibration of the movable base is produced at the time of tomography using the X-ray CT apparatus, the X-ray tube and the detector are also vibrated. As a result of this, there has been a problem that deflection or the like is produced in the X-rays to be detected by the detector, thereby degrading the image.

Thus, a method of reducing the rotation unbalance by removing the unbalance of a rotary machine by the influence coefficient method for removing the unbalance has been used. The influence coefficient method is a method in which an adjustment weight is attached to the rotary machine, measurement is performed, and then the rotation unbalance is removed.

When the influence coefficient method is used, for example, the amplitude waveform of the measured vibration data shown in FIG. 13 is subjected to fast Fourier transform (FFT) processing. Vibration which is in synchronization with the rotational speed, and is a rotation period component is obtained by the FFT processing. Then, an unbalance vector E is obtained on the basis of a phase lag of the amplitude of the vibration. Then, a test weight is attached to the rotary machine, the same processing is performed, the amplitude waveform shown in FIG. 14 is obtained, and an unbalance vector F is obtained on the basis of the amplitude of the vibration which is in synchronization with the rotational speed, and is a rotation period component, and the phase lag.

Here, assuming that the vector of the test weight is U, the influence $\alpha$ exerted on the vibration is expressed by $\alpha=(F-E)/U$. As for a corrected weight amount, it is sufficient if E becomes 0 by attaching the corrected weight amount V. Thus, $V=-E*U/(F-U)$ is obtained. By attaching this corrected weight amount V to the rotary machine, the vibration of the rotary machine is reduced.

A waveform of an example of the result obtained by removing the unbalance of the rotary machine and reducing the vibration thereof by using this influence coefficient method is shown in FIG. 16. As shown in FIG. 16, by using the influence coefficient method, it becomes possible to reduce the peak-to-valley amplitude of the vibration from about 200 to 140 µm.

As such an influence coefficient method, a method is known in which, as described in, for example, Jpn. Pat. Appln. KOKAI Publication No. 2001-170038, and Jpn. UM Appln. KOKAI Publication No. 5-70506, the weight is formed in such a manner that the weight can be moved in at least one of the radial direction and the rotational axis direction of the rotating section of the movable base, or toward the rotation center of the movable base. The method of performing balance adjustment with excellent accuracy by making the weight movable as described above is known.

Further, as described in Jpn. Pat. Appln. KOKAI Publication No. 8-214512, horizontal and vertical vibration on each of bearing brackets for rotatably supporting bearings for supporting the ends of the rotation shaft of a rotor, and the rotation shaft is measured. A method of performing balance adjustment of the rotor by minimizing the vibration on the basis of the measured vibration and an operation formula is also known.

Further, the configuration described in Jpn. Pat. Appln. KOKAI Publication No. 2005-211662 in which unbalance is measured, and a plurality of balance rings each having unbalance are included is also known. In this method, control for adjusting a position of a balance ring by a motor in accordance with predetermined algorithm for unbalance correction is performed.

There is also a method, described in Japanese Patent Application No. 2004-65477, of adjusting an angle or a distance in such a manner that a formula based on respective conditions is established. Further, as described in Jpn. Pat. Appln. KOKAI Publication No. 2005-40604, a method is also known in which a system for determining a weight and a position of the weight necessary for addition of the weight for achieving the static and dynamic balance by a test operation or a trial operation is used.

However, there has been a problem in the adjustment method and the adjustment device of balance using the influence coefficient method described above. That is, when the influence coefficient method is used, in order to obtain the position of a weight and an amount of the weight suitable for removing the rotation unbalance, first, a weight is attached to each rotary machine to perform a test operation. A corrected weight amount is obtained by this test operation. Further, it is necessary to perform an operation and measurement by attaching a corrected weight to the rotary machine on the basis of the corrected weight amount. A test operation is necessary as described above, and much time is required to conduct the work for reducing the vibration.

Further, even when the rotation unbalance is removed, there is the possibility of an amplitude increasing in the P-V (peak-to-valley) amplitude. That is, even when the rotation unbalance is removed, there is a case where vibration is caused by various factors such as rigidity of each part (for example, a bearing section), fluid impact caused by the air resistance at the time of rotation, and the like. As described above, the influence coefficient method is a method of removing rotation unbalance, and there has been the possibility of reduction in vibration being not achieved farther than a certain level even when the rotation unbalance is removed.

BRIEF SUMMARY OF THE INVENTION

As an aspect of the present invention, there is provided an adjustment device of a rotary machine including a movable base formed rotatable around an axis, characterized by comprising: a vibration measuring instrument formed in such a manner that when the movable base is rotated, the instrument can measure an amplitude of vibration of the rotary machine along each of the axis and the orthogonal to the axis; and calculation means for calculating, a position and a weight of an adjustment weight to be provided on the movable base on the basis of the amplitude measuring the vibration measuring instrument, in such a manner that a weight of the adjustment weight can be adjusted, and the adjustment weight can be moved along the axis, the position and the weight of the adjustment weight minimizing the amplitude of the movable base.

As an aspect of the present invention, there is provided an adjustment method of a rotary machine including a movable base formed rotatable around a axis, characterized by comprising: a step of measuring an amplitude of the rotary machine along the axis and the orthogonal to the axis when the movable base is rotated; a step of calculating a position and a weight of an adjustment weight by using calculation means on the basis of the measured amplitude in such a manner that the amplitude of the movable base is minimized; and a step of attaching the adjustment weight to the movable base on the basis of the position and the weight of the adjustment weight calculated by the calculation means.

As an aspect of the present invention, there is provided a manufacturing method of a rotary machine, characterized by comprising: a step of assembling a rotary machine including a movable base, and formed rotatable, and a stationary base for supporting the movable base; and a step of adjusting the assembled a rotary machine by the adjustment method of a rotary machine.

According to the present invention, it becomes possible to reduce vibration by a simple method by using an adjustment device of a rotary machine for balance adjustment of a rotary machine at the time of rotation of the rotary machine, an adjustment method of a rotary machine, and a manufacturing method of an X-ray CT apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is an explanatory view showing attaching position of weights used in the adjustment device.

FIG. 4 is an explanatory view showing the attaching positions of the weights.

FIG. 5 is a flowchart showing a flow of transverse vibration adjustment by the adjustment device.

FIG. 8 is a flowchart showing a derivation flow of a change amount and a position of an adjustment weight in the longitudinal vibration adjustment.

FIG. 9 is an explanatory view showing an example of a vibration waveform at the time of adjustment of a rotary machine.

FIG. 10 is an explanatory view showing an example of a vibration waveform at the time of adjustment of a rotary machine.

FIG. 11 is an explanatory view showing an example of an amplitude waveform at the time of adjustment of a rotary machine.

FIG. 12 is an explanatory view showing an example of an amplitude waveform at the time of adjustment of a rotary machine.

FIG. 13 is an explanatory view showing an example of an amplitude waveform at the time of adjustment of a conventional rotary machine.

FIG. 14 is an explanatory view showing an example of an amplitude waveform at the time of adjustment of the conventional rotary machine.

FIG. 15 is an explanatory view showing an example of an amplitude waveform at the time of adjustment of the conventional rotary machine.

DETAILED DESCRIPTION OF THE INVENTION

An adjustment device 1 according to an embodiment of the present invention will be described below with reference to FIGS. 1 to 12.

Figure 1:
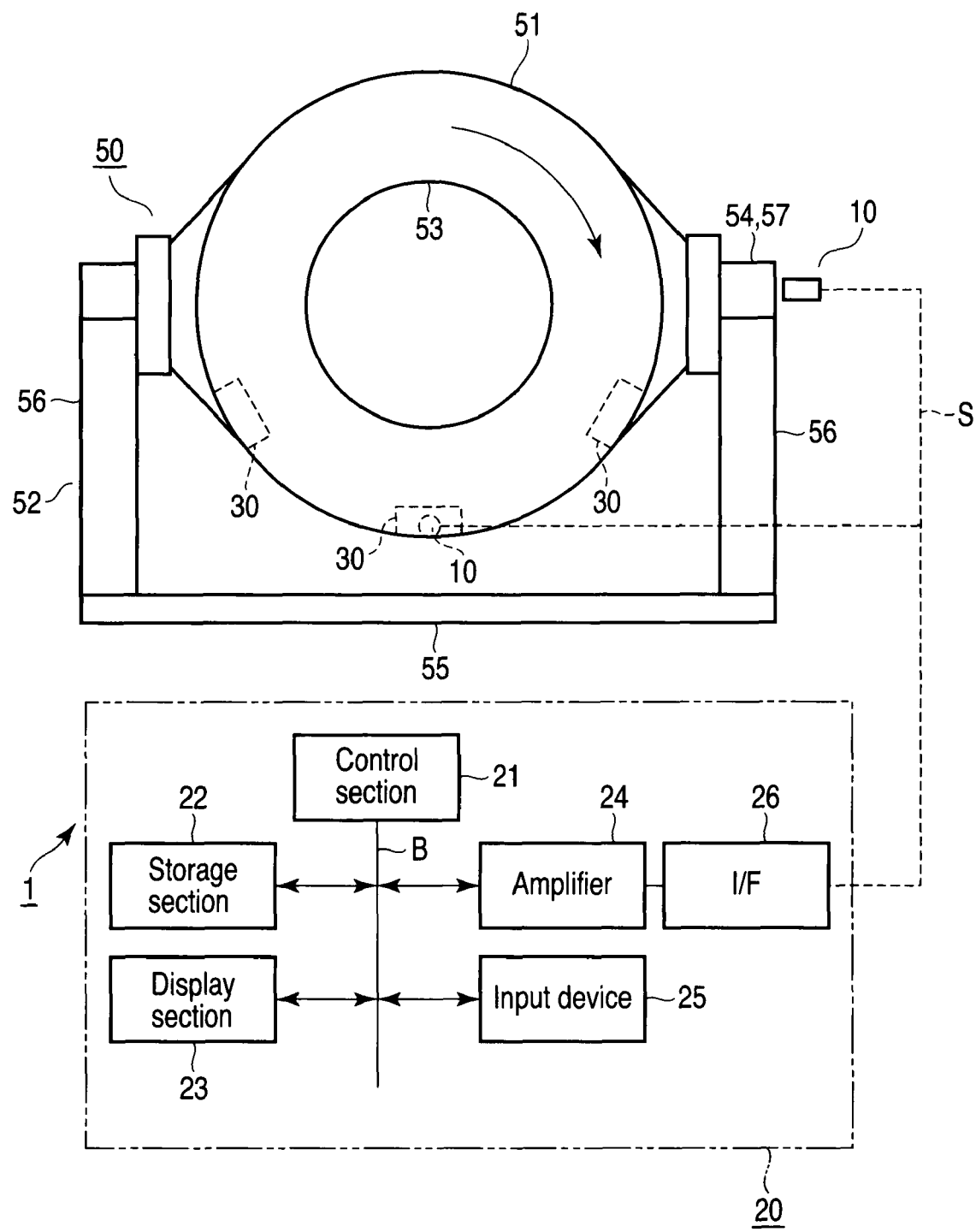
FIG. 1 is a front view showing the configuration of an adjustment device according to an embodiment of the present invention.
Figure 2:
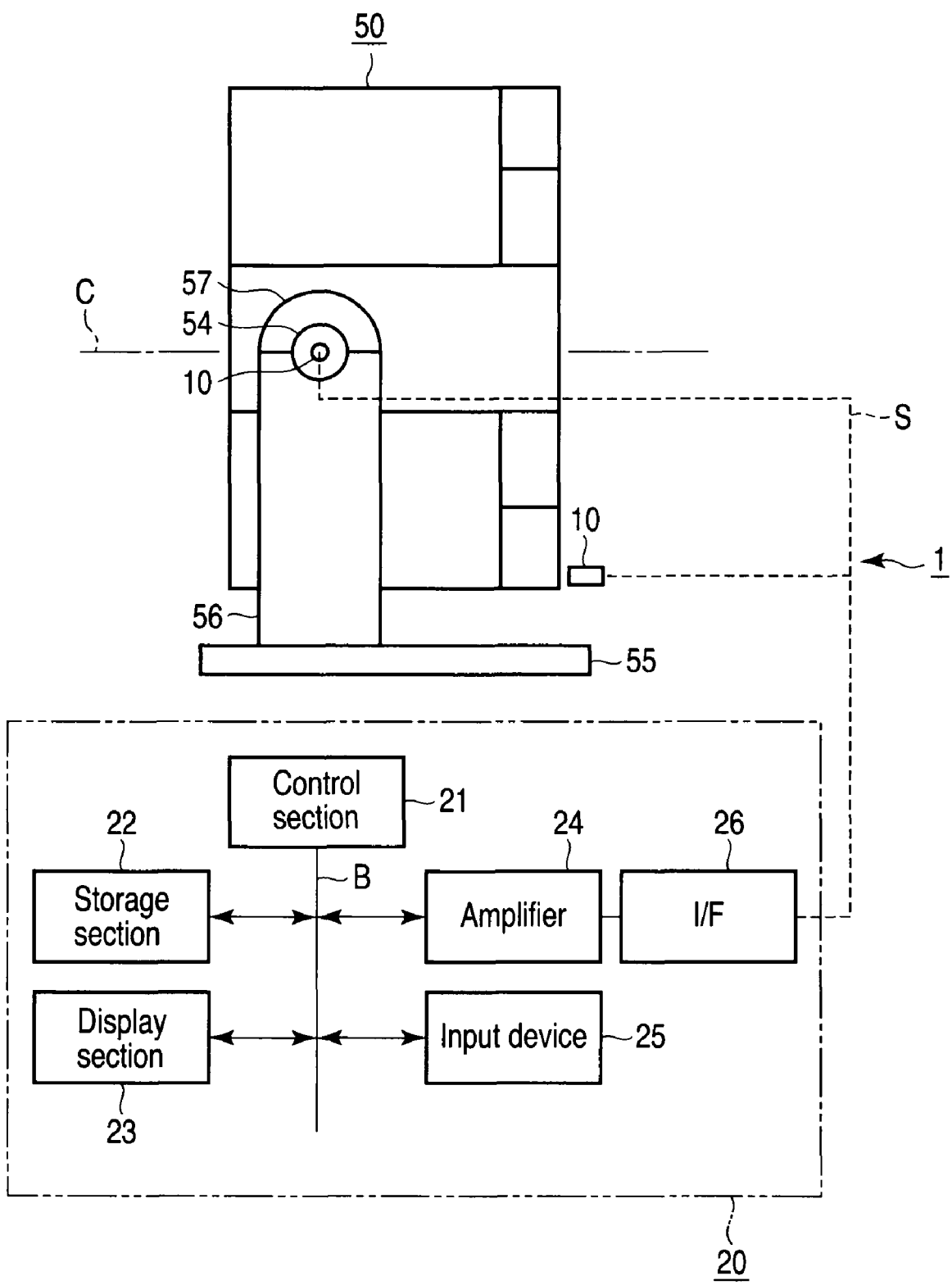
FIG. 2 is a side view showing the configuration of the adjustment device.

FIG. 1 is an explanatory view showing the configuration of an adjustment device 1 according to an embodiment of the present invention. FIG. 2 is an explanatory view showing the configuration of the adjustment device 1. FIG. 3 is an explanatory view showing attaching positions of weights 30 used in the adjustment device 1. FIG. 4 is an explanatory view showing the attaching positions of the weights 30.

As shown in FIGS. 1 and 2, the adjustment device 1 is used in a rotary machine 50. The adjustment device 1 is provided with a plurality (two in this embodiment) of vibration sensors 10, a personal computer (PC) 20, and weights (hereinafter referred to as "adjustment weights") 30 for adjusting the rotary machine 50.

The rotary machine 50 is, for example, an X-ray CT apparatus. The rotary machine 50 is provided with a movable base 51, and a stationary base 52, and is formed so that tomography of an subject can be performed.

The movable base 51 is formed into an annular shape having a hollow section 53. The movable base 51 is formed rotatable around a axis C of the movable base 51. The movable base 51 is formed so that the subject can be surrounded by the movable base 51 by moving the subject (patient or the like) into the hollow section 53. The movable base 51 is provided with an X-ray tube, and a detector opposed to the X-ray tube with the center of the movable base 51 between the X-ray tube and the detector. A plurality of adjustment weights 30 to be described later are provided at the outer circumferential section of the movable base 51. It should be noted that the movable base 51 is formed movable by the direct drive system, the belt system, or the like.

Further, the movable base 51 is provided with a support shaft 54 on a horizontal line passing radially through the center of the movable base 51, and at a position shifted from the center in the thickness direction thereof to the one side thereof. As shown in FIGS. 3 and 4, the movable base 51 is provided with a plurality of storage sections 60 for fixing the adjustment weights 30.

The stationary base 52 is provided with a flat base 55 to be placed on, for example, a floor surface, stands 56 provided at both ends of the flat base 55, and support sections 57 provided at upper parts of the stands 56, and supporting the support shaft 54.

In the rotary machine 50, the subject is moved to the hollow section 53 of the movable base 51 at the operation time of the rotary machine 50. Further, the rotary machine 50 is formed in such a manner that the detector can be irradiated with the X-rays from the X-ray tube through the subject. At this time, in order to form, for example, a cross section by passing the X-rays through the subject, the movable base 51 is formed so that it can be rotated at a rate of, for example, less than 0.35 s to 1.0 s/rev.

As shown in FIGS. 3 and 4, when one vertex of the movable base 51 is assumed to be at a 0° position, the storage sections 60 are provided at three positions of 120°, 180°, and 240°. Further, each of the storage sections 60 at the three positions is provided at two positions separate from each other in the thickness direction of the movable base 51 by a predetermined distance t, for example, 0.1 m.

As the vibration sensor 10, for example, that of a noncontact type is used. The vibration sensors 10 are connected to the PC 20 through a signal line S. The vibration sensors 10 are provided in close proximity to each of one of the support sections 57 of the rotary machine 50, and the lower end of one surface of the movable base 51. The vibration sensor 10 is formed so that it can measure the amplitude of the rotary machine 50 as the transverse vibration and the longitudinal vibration of the rotary machine 50. In other words, the vibration sensor 10 is formed so that it can measure the transverse vibration which is orthogonal to the axis C of the movable base 51 and the longitudinal vibration which is along the axis C of the movable base 51.

It should be noted that the vibration sensor 10 may be of a contact type if it can measure the amplitude at each phase (angle) of the rotary machine 50. Further, the measurement position can also be set appropriately. Further, for the convenience of explanation, one side of the movable base on which the vibration sensor 10 is provided is defined as the back of the rotary machine 50, and the other side is defined as the front of the rotary machine 50.

The PC 20 is provided with a control section 21 such as a central processing unit (CPU) or the like. Further, the PC 20 is provided with a storage section 22, a display section (output means) 23 such as a display or the like for displaying information such as waveform data and the like, an amplifier 24, and an input device 25 such as a keyboard and a mouse for inputting external information. These structural elements of the PC 20 are connected to the control section 21 through a bus line B, such as an address bus or a data bus. It should be noted that the PC 20 formed in such a manner that the PC 20 has the configuration including the functions of a vibration measuring instrument, and calculation means (derivation means and operation means) by the control section 21, storage section 22, and amplifier 24. It should be noted that a configuration other than the PC 20 may be used if the configuration includes calculation means.

The storage section 22 is provided with a read only memory (ROM) in which fixed data such as a program is stored in advance, and a random access memory (RAM) in which a storage area for storing necessary data such as a predetermined function and the like is formed. The display section 23 is formed so that it can appropriately display influence wave data items, an amount of change in the adjustment weight 30, and the like to be described later.

The amplifier 24 is connected to the signal line S through an interface 26, and receives a signal of the vibration sensor 10 through the signal line S and the interface 26. Further, the amplifier 24 is formed so that it can perform amplification and conversion of the signal.

The plurality of adjustment weights 30 are provided in the storage sections 60 of the movable base 51, and are formed so that they can be moved or increased/decreased in the number. It should be noted that at the time of manufacture of the movable base 51, a predetermined number of the adjustment weights 30 are arranged in advance in the storage sections 60.

An adjustment method of the rotary machine 50 using the adjustment device 1 configured as described above will be described below with reference to the flowcharts of FIGS. 5 to 8. It should be noted that this adjustment method relates to adjustment of transverse balance and longitudinal balance for reducing transverse vibration and longitudinal vibration produced by the rotation of the movable base 51 at the time of the operation of the rotary machine 50. Here, the transverse vibration is vibration that occurs in the direction horizontally orthogonal to the axis C of the movable base 51. In other words, the transverse vibration is the vibration produced in the radial direction of the movable base 51. Further, the longitudinal vibration is vibration that occurs in the direction of the axis C of the movable base 51. In other words, the longitudinal vibration is the vibration produced in the thickness direction of the movable base 51. In this adjustment method, it is specified that after adjustment of the transverse vibration, the longitudinal vibration is adjusted. Further, as an evaluation criterion for evaluating reduction in vibration, a peak-to-valley (P-V) amplitude from the uppermost point (peak) of the vibration waveform (vibration data) to the lowermost point (valley) is made the subject of the evaluation.

First, as the transverse vibration adjustment of the movable base 51, electric power is supplied to the manufactured rotary machine 50, and the movable base 51 is rotated. Then, data (hereinafter referred to as "vibration data" corresponding to first adjustment vibration data) $A_n$ of the vibration (vibration at each phase) produced by the rotation of the movable base 51 is measured by means of the vibration sensor 10 provided at the one support section 57 of the rotary machine 50 (step ST11).

A signal of the vibration data measured by the vibration sensor 10 is transmitted to the amplifier 24 of the PC 20 through the signal line S. Upon receipt of the signal through the amplifier 24, the control section 21 of the PC 20 instructs the amplifier 24 to amplify the signal. Further, the signal amplified by the amplifier 24 is stored (memorized) in the storage area of the storage section 22. The control section 21 activates a program provided in the storage section 22, and subjects the amplitude data stored in the storage section 22 to waveform processing by using the program, thereby forming a waveform of the rotary machine 50 shown in FIG. 9.

In the vibration waveform of the rotary machine 50 shown in FIG. 9, the ordinate indicates the displacement (μm), and the abscissa indicates the phase (degree). It should be noted that the adjustment weights 30 described here are in the state where they are arranged at the time of manufacture, and are associated with the vibration data $A_n$ of the rotary machine 50 provided with the adjustment weights 30 of the rotary machine 50 in the initial state. It should be noted that n indicates the number of times of movement or installation of the adjustment weights 30. Accordingly, in the vibration data $A_n$ in this state (step ST11), the adjustment weights 30 of the movable base 51 are provided at the time of manufacture, and movement or installation of the adjustment weights 30 is not performed yet, and hence n=0. As a result of this, the vibration data becomes $A_0$.

Then, an adjustment weight 30 arranged in one of the storage sections 60 of the movable base 51 is arbitrarily moved or an adjustment weight 30 is newly arranged in one of the storage sections 60 (step ST12). That is, an adjustment weight 30 of an arbitrary weight $x_0$ is arranged at an arbitrary angle $\theta_{A0}$. Here, the adjustment weight is adjusted one time, and hence the number of times of movement/installation n becomes 1 (n=1) (step ST13).

In this state, vibration data $A_1$ (corresponding to second adjustment vibration data) of the rotary machine 50 is measured in the same manner as the vibration data $A_0$ described previously (step ST14). The measured vibration data $A_1$ is also subjected to the waveform processing by the control section 21 in the same manner as the vibration data $A_0$, whereby the waveform shown in FIG. 10 is formed.

It becomes possible to express such vibration data (waveform) in the form of a function of the change amount x and the position (angle) $\theta_A$ of the adjustment weight 30 by the difference in the adjustment weight 30 between before and after the change (for example, between the vibration data $A_0$ and the vibration data $A_1$). For example, as for the vibration data (waveform), waveform data (hereinafter referred to as an "influence wave" corresponding to the first influence wave data) influenced by the change amount x and the position $\theta_A$ of the adjustment weight 30 is expressed by the function $f_A(x, \theta_A)$.

Assuming the prechange waveform of the adjustment weight 30 to be $A_{n-1}$, and the postchange waveform thereof to be $A_n$, the influence wave (function) $f_A(x, \theta_A)$ is expressed by the following formula, and the control section 21 of the PC 20 calculates the function $f_A(x, \theta_A)$ from the formula (step ST15).

$$f_A(x, \theta_A) = A_n - A_n - A_{n-1}$$

At this time, the control section 21 calculates this function $f_A(x, \theta_A)$ from the vibration data $A_0$, and $A_1$ obtained in steps ST11 and ST14 of the transverse balance adjustment. Then the control section 21 stores the function $f_A(x, \theta_A)$ of the transverse balance obtained by $f_A(x, \theta_A) = A_1 - A_0$ in the storage section 22, and subjects the function to the waveform processing to obtain the waveform data shown in FIG. 11.

It should be noted that the function $f_A(x, \theta_A)$ can be approximated by $f_A(x, \theta A) = \alpha 1 \cdot x \cdot \cos(\omega + \alpha_2 + \theta_A)$ using coefficients of $\alpha_1$ and $\alpha_2$ as an example. By approximating the function $f_A(x, \theta_A)$ by the approximate expression, it becomes possible for the control section 21 to perform waveform processing of the influence wave data (corresponding to the first approximate influence wave data) in the change amount x and the position $\theta_A$. It should be noted that $\alpha_1$ and $\alpha_2$ are coefficients to be changed in each state, and can be appropriately set in accordance with the shape, use condition, and the like of the movable base 51. In this embodiment, when an adjustment weight 30 of 5 kg is added to the storage section 60 provided at the 120° position of the movable base 51, the change amount x and the position (angle) $\theta_A$ become as follows. x=5 (kg), $\theta_A$=120 (°) That is, the approximate expression is obtained (derived) from the actually measured function $f_A(x, \theta_A)$.

Then, the control section 21 obtains (calculates) a change amount $x_{min}$ and a position (angle) $\theta_{min}$ from the approximate expression as variables that minimize the P-V amplitude when vibration data $A_n$ is added to the obtained function $f_A(x, \theta_A)$ (step ST16).

A flow for deriving the change amount $x_{min}$ and the position (angle) $\theta_{min}$ that minimize the P-V amplitude will be described below with reference to the variable determination flow of FIG. 6.

Figure 6:
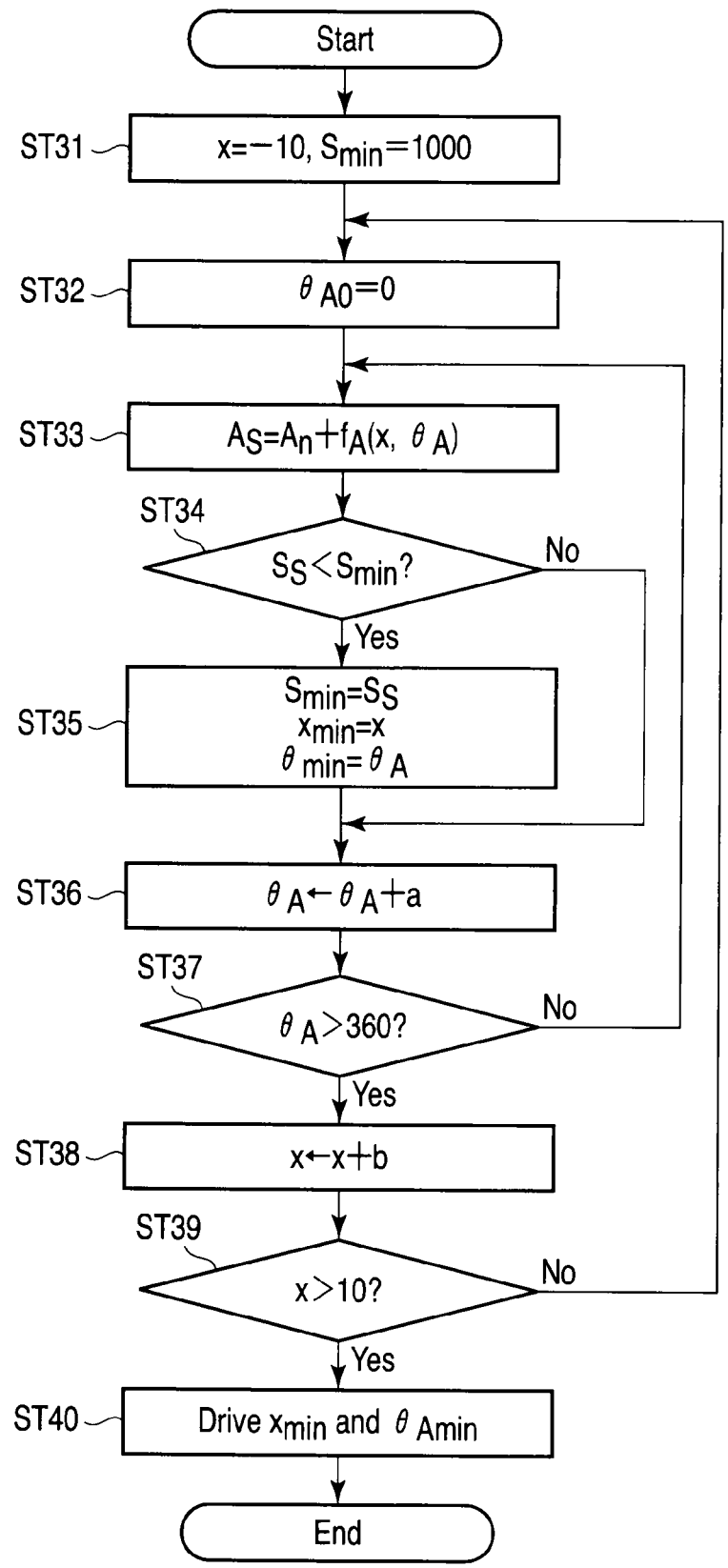
FIG. 6 is a flowchart showing a derivation flow of a change amount and a position of an adjustment weight in the transverse vibration adjustment.

As shown in FIG. 6, first, the control section 21 activates a variable determination program (operation means) for obtaining a variable by the approximate expression stored in the storage section 22. Then, the control section 21 inputs the change amount x of the minimum value (or maximum value) of one of a weight that enables movement of the adjustment weight 30, and a weight that enables an increase/decrease of the adjustment weight 30, and an arbitrary value of the P-V amplitude $S_{min}$ as initial values from the input device 25 (step ST31). Then, the control section 21 inputs the position (angle) $\theta_A$ of the adjustment weight 30 (step ST32). It should be noted that the variable determination program is that for performing the processing of steps ST31 to ST40 (or steps ST71 to ST80 to be described later).

Here, as an example, the minimum value and the maximum value of the change amount of the adjustment weight 30 are set as x=−10 to +10 kg, the position θA is set as θA=0 to 360°, and the P-V amplitude $S_{min}$ is set at 1000. That is, the control section 21 calculates the P-V amplitude $S_{min}$ that minimizes within the range of the change amount x and the position $\theta_A$ by using the variable determination program, i.e., the approximate expression. Accordingly, the change amount x=−10, the position $\theta_A$=0, and $S_{min}$=1000 are input as the initial values of the variable determination program.

Then, the control section 21 calculates the combined wave $A_S$ by the variable determination program (step ST33). It should be noted that $A_S$ is expressed by $A_S = A_1 + f_A(X, \theta_A)$. From this formula, the combined wave As is obtained, and the P-V amplitude $S_S$ of the combined wave $A_S$ is measured.

The control section 21 compares the obtained P-V amplitude $S_S$ and the P-V amplitude $S_{min}$ substituted as the initial value with each other (step ST34). Here, when $S_S$ is smaller than $S_{min}$, the P-V amplitude $S_{min}$, the change amount $x_{min}$, and the position $\theta_{min}$ are replaced with Pmin=$P_S$, xmin=x, and $\theta_{min}=\theta_A$, respectively as the procedure for YES of step ST34 (step ST35). It should be noted that when $S_S$ is larger than $S_{min}$, replacement of the P-V amplitude $S_{min}$, the change amount $x_{min}$, and the position $\theta_{min}$ is not performed as the procedure for NO of step ST34.

Then, by setting a position obtained by adding a divided amount a to the position (angle) $\theta_A$ as the new position $\theta_A$ ($\theta_A \leftarrow \theta_A + a$), the position $\theta_A$ is newly set (resetting) (step ST36). It should be noted that when the divided amount a is, for example, 5°, in the case of ST36 of the first time, $\theta_A$ becomes 5° ($\theta_A = 0 + 5 = 5°$).

After setting $\theta_A$ again, it is determined whether or not $\theta_A$ is larger than 360° (step ST37). When $\theta_A$ is smaller than 360° as a result of the determination, the flow is returned to step ST33 again as the procedure for NO of step ST37, a new position $\theta_A$ is set, and the combined wave $A_S$ is calculated. Thereafter, the same processing is performed. This processing is repeated until the position $\theta_A$ becomes larger than 360°. It should be noted that although the determination criterion is set as $\theta_A > 360°$ here, this is the maximum value of the variable $\theta_A$.

Then, when $\theta_A$ becomes larger than 360°, a new change amount obtained by adding a divided amount b to the change amount x is set as x ($x \leftarrow x + b$) as the procedure for YES of step ST37, whereby the change amount x is newly set (resetting) (step ST38). It should be noted that the divided amount b is, for example, 1 kg. In this case, in step ST38 of the first time, x becomes −9 (x=−10+1=−9).

After setting x again, it is determined whether or not x is larger than 10 kg (step ST39). When x is smaller than 10 kg as a result of this determination, the flow is returned to step ST32 again, a new change amount x is set, and the combined wave As is calculated as the procedure for NO of step ST39. Thereafter, the same processing is performed. The same processing is repeated using the new change amount x until the position $\theta_A$ becomes 360°, thereafter the change amount x is set again, and the processing is repeated until x becomes larger than 10. It should be noted that although the determination criterion is set as x>10 kg here, this is the maximum value of the change amount, and it is sufficient if the determination criterion is one of the minimum value and the maximum value of the change amount x.

Then, when x becomes larger than 10 kg, the result of step ST39 becomes YES, and $x_{min}$ and $\theta_{min}$ at the time of the replaced minimum P-V amplitude $S_{min}$ are derived (step ST40).

When the minimum values of the change amount $x_{min}$ and the position $\theta_{min}$ are derived, the flow is returned to the flowchart of FIG. 5, and adjustment of the adjustment weight 30 for arranging an adjustment weight 30 based on the change amount $x_{min}$ and the position $\theta_{min}$ on the movable base 51 is performed (step ST17).

The procedure for arrangement of the adjustment weight 30 performed to adjust the transverse vibration of the above-mentioned movable base 51 will be described below.

First, parameters of the change amount $x_{min}$ and the position (angle) $\theta_{Amin}$ of the influence wave $f_A(x_{min}, \theta_{Amin})$ that minimize the P-V amplitude $S_{min}$ derived by step ST16 described above are displayed on the display section 23 of the PC 20. Then, the parameters of the change amount and the position are vector-resolved with respect to at least two positions of the plural storage sections 60 provided on the movable base 51.

For example, the case where the parameters derived in step ST16 described above are a change amount $x_{min} = -3$ kg, and a position (angle) $\theta_{Amin} = 165°$ will be described below. As for the adjustment of the adjustment weight 30 of the storage section 60, the adjustment weights 30 of the storage sections 60 provided at 120° and 180° positions between which the 165° position is located are adjusted. Accordingly, when −3 kg provided at the 165° position is vector-resolved with respect to the storage sections 60 provided at the 120° and 180° positions, (−3 kg, 165°)=(−0.9 kg, 120°)+(−2.45 kg, 180°) is obtained.

That is, the adjustment weights 30 provided in advance in the respective storage sections 60 are adjusted in the following manner. In the storage section provided at the 120° position, the adjustment weight 30 is reduced by 0.9 kg. Further, in the storage section provided at the 180° position, the adjustment weight 30 is reduced by 2.45 kg. That is, the adjustment weight at the 120° position is reduced by 0.9 kg, and the adjustment weight at the 180° position is reduced by 2.45 kg, whereby the same effect as reducing the adjustment weight at the 165° position by 3 kg can be obtained. It should be noted here that the sign + of the change amount x of the adjustment weight 30 indicates addition of the adjustment weight 30, and the sign − indicates reduction.

After adjusting the adjustment weights 30 in step ST17 in this manner, the adjustment weights are rearranged, and hence n is increased by one (n=n+1) (step ST18). It should be noted that when the adjustment of the adjustment weight 30 in step ST17 is the first time after step ST12, n becomes 2 (n=1+1=2).

Subsequently, vibration data $A_n$ (n=2) is measured in the same manner as step ST14 (step ST19). After the vibration data $A_2$ is measured, it is determined whether or not the vibration data $A_2$ is within an allowable range (step ST20). Here, as the contents of the determination whether or not the vibration data $A_2$ is within an allowable range, for example, the P-V amplitude of the vibration data $A_2$ and a predetermined P-V amplitude (target amplitude set in each rotary machine 50) are compared with each other. Here, when the P-V amplitude of the vibration data $A_2$ is smaller than the predetermined P-V amplitude, it is determined that the vibration data $A_2$ is within the allowable range (YES in step ST20), the adjustment of the transverse vibration is completed.

When the P-V amplitude of the vibration data $A_2$ is larger than the predetermined P-V amplitude, it is determined that the vibration data $A_2$ is out of the allowable range (NO in step ST20), and the flow is returned to step ST15. When the flow is returned to step ST15, the function $f_A(x, \theta_A)$ is calculated again from $f_A(x, \theta_A) = A_n - A_{n-1}$ on the basis of the change amount x and the position $\theta$ of $A_n$ (n=2) calculated by the adjustment. It should be noted that the same processing as steps ST15 to ST19 is repeated until the result of step ST20 becomes YES.

Figure 7:
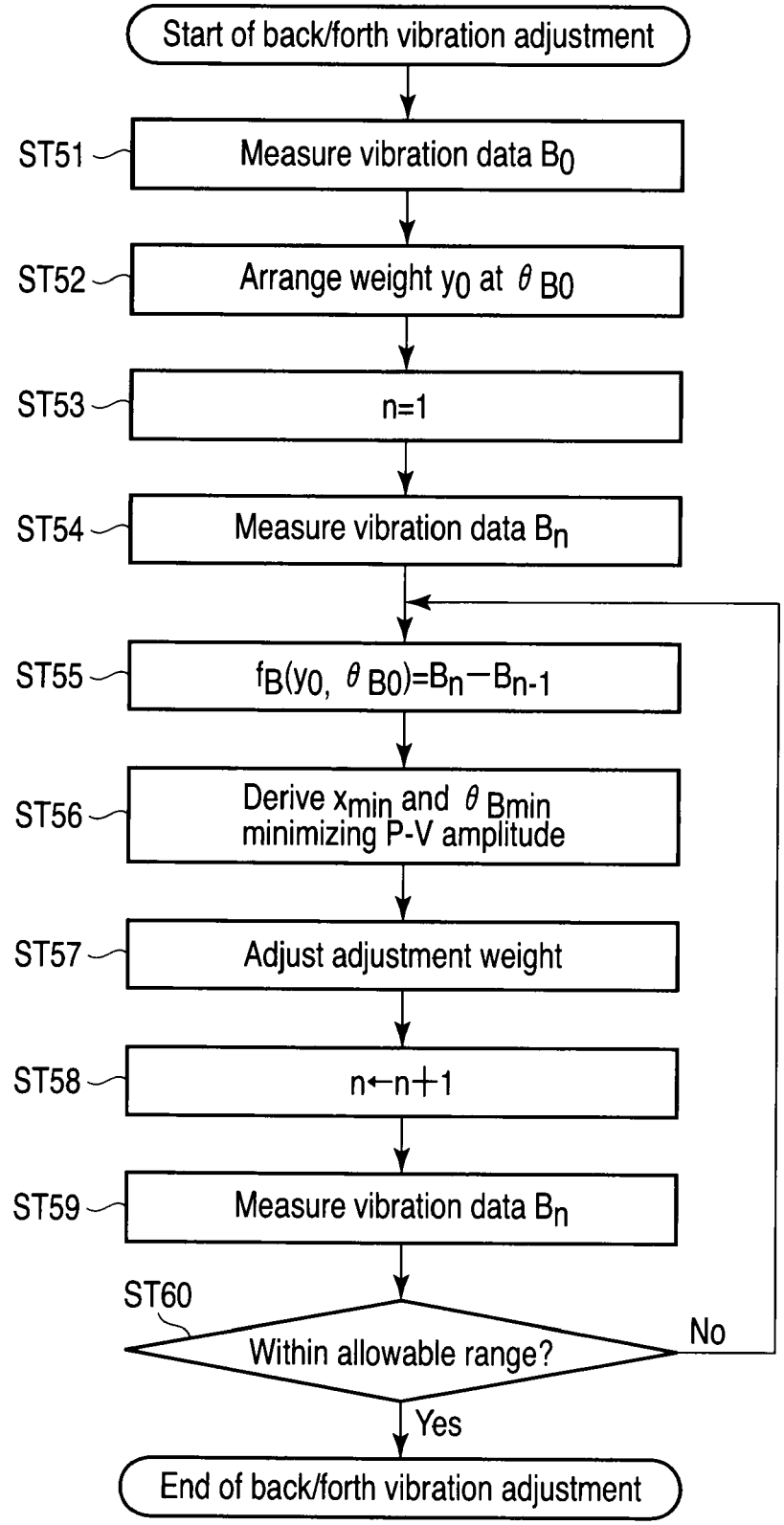
FIG. 7 is a flowchart showing a flow of longitudinal vibration adjustment by the adjustment device.

Subsequently, when the P-V amplitude of the vibration data $A_n$ becomes smaller than the predetermined P-V amplitude, and the transverse balance adjustment is completed as the result YES of step ST20, the adjustment of the longitudinal vibration shown in the flowchart of FIG. 7 is performed.

First, as the longitudinal vibration adjustment of the movable base 51, the movable base 51 of the rotary machine 50 that has already been subjected to the transverse balance adjustment described above is rotated. Subsequently, the vibration data (corresponding to third adjustment vibration data) $B_n$ produced by the rotation of the movable base 51 is measured by means of the vibration sensor 10 provided in close proximity to the lower end of the one surface of the movable base 51 (step ST51). It should be noted that n indicates the number of times of movement or installation of the adjustment weight 30. Accordingly, in the vibration data $B_n$ in this state (step ST51), the adjustment weights 30 have not been moved, and hence the vibration data becomes the vibration data $B_n$ of the rotary machine 50 provided with the adjustment weights 30 of the rotary machine 50 arranged at the time of the longitudinal vibration adjustment. At this time, the adjustment weights 30 are those provided at the time of the transverse balance adjustment, and movement or installation of the adjustment weights is not performed yet. That is, n=0, and hence the vibration data becomes $B_0$.

A signal of the amplitude data measured by the vibration sensor 10 is transmitted to the amplifier 24 of the PC 20 through the signal line S. When the amplifier 24 receives this signal, the control section 21 of the PC 20 instructs the amplifier 24 to amplify the signal, and stores the amplified signal in the storage area of the storage section 22. The control section 21 forms the waveform of the amplitude data stored in the storage section 22. For example, the control section activates the program provided in the storage section 22, and subjects the amplitude data to waveform processing by the program, whereby the waveform of the data is formed.

Subsequently, the adjustment weight 30 arranged in the movable base 51 of the rotary machine 50 is arbitrarily moved axially relative to the movable base 51 (step ST52). In this movement, an adjustment weight 30 in one of the storage sections 60 provided at the respective angle positions is moved axially. That is, an adjustment weight 30 at an arbitrary angle $\theta_{B0}$ is changed by an arbitrary change amount $y_0$. It should be noted that the change amount y is a variable obtained by moving an adjustment weight 30 having a certain weight w a certain distance 1 axially, and the unit of the change amount y is, for example, y (kg·m). Here, the adjustment weight 30 has been adjusted once, and hence n becomes 1 (n=1) (step ST53).

In this state, the vibration data (corresponding to fourth adjustment vibration data) $B_n$ (n=1) of the rotary machine 50 is measured in the same manner as the vibration data $B_0$ described above (step ST54). The measured vibration data B1 is also subjected to the waveform processing by the control section 21 in the same manner as the vibration data $B_0$, and the waveform is formed by the PC 20.

Such vibration data is expressed by a function of the change amount y and the position (angle) $\theta_B$ of the adjustment weight on the basis of the difference between before and after the change of the adjustment weight 30 (for example, vibration data $B_0$, $B_1$). That is, regarding the vibration data, the influence wave (second influence wave data) of the change amount y and the position θ of the adjustment weight 30 can be expressed by the function $f_B(y, \theta_B)$.

Assuming that the waveform of the adjustment weight 30 before the change is $B_{n-1}$, and the waveform thereof after the change is $B_n$, the influence wave data (function) $f_B(y, \theta_B)$ is expressed by the following formula, and the control section 21 of the PC 20 calculates the function $f_B(y, \theta_B)$ from this formula (step ST55).

$$f_B(y, \theta_B) = B_n - B_{n-1}$$

At this time, the control section 21 calculates the function $f_B(y, \theta_B)$ on the basis of the vibration data $B_0$ and $B_1$ obtained in steps ST51 and ST54 of the longitudinal vibration adjustment. Then, the control section 21 subjects the waveform data of the function $f_B(y, \theta_B)$ of the longitudinal balance obtained by $f_B(y, \theta_B) = B_1 - B_0$ to waveform processing.

It should be noted that the function $f_B(y, \theta_B)$ can be approximated by $f_B(y, \theta_B) = \beta_1 \cdot y \cdot \cos(\omega + \beta_2 + \theta_B)$ using coefficients of $\beta_1$ and $\beta_2$ as an example. By approximating the function $f_B(y, \theta_B)$ by the approximate expression, it becomes possible for the control section 21 to perform waveform processing of the influence wave data (corresponding to the second approximate influence wave data) in the change amount y and the position $\theta_B$. It should be noted that $\beta_1$ and $\beta_2$ are coefficients to be changed in each state, and can be appropriately set in accordance with the shape, and the like of the movable base 51.

Further, when the axial movement distance of the adjustment weight 30 is constant, it becomes also possible to include the movement distance in the coefficient $\beta_1$, and make the dimension of the change amount y the weight (kg). This becomes possible when, for example, all the distances of the plurality of storage sections 60 provided axially at the respective positions (angles) of the movable base 51 of this embodiment are constant. When the axial distance of the storage section 60 is 0.1 m, the change amount y (kg·m) is a change amount constituted of weight w and distance 1, and by including the movement distance term in the coefficient $\beta_1$, the following is obtained.

$$\beta_3 = \beta_1 \cdot 1 = 0.1\beta_1$$

$$y' = y/\beta_3$$

As a result of this, the function $f_B(y', \theta_B)$ becomes as follows.

$$f_B(y', \theta_B) = \beta_3 \cdot y' \cdot \cos(\omega + \beta_2 + \theta_B)$$

In this embodiment, the distance of the storage section 60 is 0.1 m (t=0.1 m), and hence the change amount y' becomes 10y (y'=10y).

That is, when an adjustment weight 30 of 5 kg is moved 0.1 m from the back to the front inside the storage section 60 provided at the 120° position of the movable base 51, the change amount y'=5 kg, and the position (angle) θB=120° are obtained.

Then, the control section 21 obtains the change amount $y'_{min}$ and the position (angle) $\theta_{Bmin}$ as variables that minimize the P-V amplitude when the vibration data $B_n$ is added to the function $f_B(y', \theta_B)$ (step ST56).

The flow for deriving the change amount $y'_{min}$ and the position (angle) $\theta_{Bmin}$ that minimize the P-V amplitude will be described below with reference to the variable determination flow of FIG. 8.

First, the control section 21 activates the variable determination program stored in the storage section 22. Then, the control section 21 inputs the minimum value (or maximum value) of one of a weight enabling movement of the adjustment weight 30, and a weight enabling an increase/decrease thereof, and an arbitrary value of the P-V amplitude $S_{min}$ as initial values by means of the input device 25 (step ST71). Then, the control section 21 inputs the position (angle) $\theta_B$ of the adjustment weight 30 (step ST72).

Here, as an example, the minimum value and the maximum value of the change amount y of the adjustment weight 30 are set as y=−1 kg·m to +1 kg·m, the position $\theta_B$ is set as $\theta_B$=0 to 360°, and the P-V amplitude $S_{min}$ is set as P-V amplitude $S_{min}$=1000. It should be noted that when the distance in the storage section 60 at each position is 0.1 m, the adjustment weight 30 is moved a fixed distance of 0.1 m, and hence the change amount y' becomes y'=−10 kg to +10 kg. Further, the divided amount c of the position $\theta_B$ is set as c=5°, and the divided amount d of the change amount y' is set as d=1 kg.

As a result of this, as the respective initial values of the variable determination program of the PC 20, the change amount y'=−10, the position $\theta_B$=0, and $S_{min}$=1000 are input.

The control section 21 calculates the combined wave $B_S$ by the variable determination program (step ST73). It should be noted that the combined wave $B_S$ is expressed by $B_S = B_1 + f_B(x, \theta_B)$. The combined wave $B_S$ is obtained from this formula, and the P-V amplitude $S_S$ of the combined wave $B_S$ is measured.

Then, the control section 21 compares the obtained P-V amplitude $S_S$ and the P-V amplitude $S_{min}$ substituted as the initial value with each other (step ST74). Here, when $S_S$ is smaller than $S_{min}$, the P-V amplitude $S_{min}$, the change amount y'$_{min}$, and the position min are replaced with S$_{min}$=S$_S$, y'$_{min}$=y', and θ$_{min}$=θ$_B$, respectively as the procedure for YES of step ST74 (step ST75). It should be noted that when S$_S$ is larger than S$_{min}$, replacement of the P-V amplitude S$_{min}$, the change amount y'$_{min}$, and the position θ$_{min}$ is not performed as the procedure for NO of step ST74.

Then, by setting a position obtained by adding a divided amount c to the position (angle) θ$_B$ as the new position θ$_B$ (θ$_B$←θ$_B$+c), the position θ$_B$ is newly set (resetting) (step ST76). It should be noted that when the divided amount c is, for example, 5°, in the case of ST76 of the first time, θ$_B$ becomes 5° (θ$_B$=0+5=5°).

After setting θ$_B$ again, it is determined whether or not θ$_B$ is larger than 360° (step ST77). When θ$_B$ is smaller than 360° as a result of the determination, the flow is returned to step ST73 again as the procedure for NO of step ST77, a new position θ$_B$ is set, and the combined wave B$_S$ is calculated. Thereafter, the same processing is performed. This processing is repeated until the position θ$_B$ becomes 360°. It should be noted that although the determination criterion is set as θ$_B$>360° here, this is the maximum value of the variable θ$_B$.

Then, when θ$_B$ becomes larger than 360°, the result of step ST77 becomes YES. Then, a new change amount obtained by adding a divided amount d to the change amount y' is set as y' (y'←y'+d), whereby the change amount y' is newly set (resetting) (step ST78). That is, in step ST78 of the first time, y' becomes −9 kg (y'=−10+1=−9 kg).

After setting y' again, it is determined whether or not y' is larger than 10 kg (step ST79). When y' is smaller than 10 kg as a result of this determination, the flow is returned to step ST72 again, a new change amount y' is set, and the combined wave B$_S$ is calculated as the procedure for NO of step ST79. Thereafter, the same processing is performed. The same processing is repeated using the new change amount y' until the position θ$_B$ becomes 360°, thereafter the change amount y' is set again, and the processing is repeated until y' becomes larger than 10. It should be noted that although the determination criterion is set as y'>10 kg here, this is the maximum value of the change amount y'. It is sufficient if the determination criterion is one of the minimum value and the maximum value of the change amount y'.

Then, when y' becomes larger than 10 kg, the result of step ST79 becomes YES, and y'$_{min}$ and θB$_{min}$ at the time of the replaced minimum P-V amplitude S$_{min}$ are derived (step ST80).

When the minimum values of the change amount y'min and the position θ$_{Bmin}$ are derived, the flow is returned to the flowchart of FIG. 7, and adjustment of the adjustment weight 30 for arranging an adjustment weight 30 based on the change amount y'min and the position θ$_{Bmin}$ on the movable base 51 is performed (step ST57).

The procedure for arrangement of the adjustment weight 30 performed to adjust the longitudinal vibration of the above-mentioned movable base 51 will be described below.

Parameters of the change amount y'min and the position (angle) θ$_{Bmin}$ Of the influence wave f$_B$(y'$_{min}$, θ$_{Bmin}$) that minimize the P-V amplitude S$_{min}$ calculated by step ST56 described above are displayed on the display section 23 of the PC 20. Then, the parameters of the change amount y'min and the position θ$_{Bmin}$ are vector-resolved with respect to at least two positions of the plural storage sections 60 provided on the movable base 51.

For example, the case where the parameters derived in step ST56 described above are a change amount y'$_{min}$=5 kg, and a position (angle) θ$_{min}$=220° will be described below. As for the adjustment of the adjustment weight 30 of the storage section 60, the adjustment weights 30 of the storage sections 60 provided at 180° and 240° positions between which the 220° position is located are adjusted. Accordingly, when 5 kg provided at the 220° position is vector-resolved with respect to the storage sections 60 provided at the 180° and 240° positions, (5 kg, 220°)=(2 kg, 1800)+(3.7 kg, 240°) is obtained.

That is, the adjustment weights 30 provided in advance in the respective storage sections 60 are adjusted in the following manner. In the storage section 60 provided at the 180° position, the adjustment weight 30 of 2 kg is moved, and in the storage section 60 provided at the 240° position, the adjustment weight 30 of 3.7 kg is moved. The adjustment weight 30 of 2 kg at the 180° position is moved forward 0.1 m, and the adjustment weight 30 of 3.7 kg at the 240° position is moved forward 0.1 m. As a result of this, the same effect as removing the adjustment weight of 5 kg at the 220° position can be obtained. It should be noted here that the sign + of the change amount y' of the adjustment weight 30 indicates forward movement of the adjustment weight 30, and the sign − indicates backward movement.

After adjusting the adjustment weights 30 in step ST57 in this manner, the adjustment weights are rearranged, and hence n is increased by one (n=n+1) (step ST58). It should be noted that when the adjustment of the adjustment weight 30 in step ST58 is the first time, n becomes 2 (n=1+1=2).

Subsequently, vibration data B$_n$ (n=2) is measured in the same manner as step ST54 (step ST59). After the vibration data B$_2$ is measured, it is determined whether or not the vibration data B$_2$ is within an allowable range (step ST60). Here, as the contents of the determination whether or not the vibration data B$_2$ is within an allowable range, for example, the P-V amplitude of the vibration data B$_2$ and a predetermined P-V amplitude are compared with each other. Here, when the P-V amplitude of the vibration data B$_2$ is smaller than the predetermined P-V amplitude, it is determined that the vibration data B$_2$ is within the allowable range (YES in step ST60), and the adjustment of the longitudinal balance is completed.

When the P-V amplitude of the vibration data B$_2$ is larger than the predetermined P-V amplitude, it is determined that the vibration data B$_2$ is out of the allowable range (NO in step ST60), and the flow is returned to step ST55. The function f$_B$(x, θ$_B$) is calculated again from f$_B$(x, θ$_B$)=B$_n$−B$_{n-1}$ on the basis of the change amount x and the position θ$_B$ of B$_n$ (n=1) calculated by the adjustment as the maximum values. It should be noted that after step ST55, the same processing as steps ST55 to ST60 is repeated until the result of step ST60 becomes YES.

Subsequently, when the P-V amplitude of the vibration data B$_n$ becomes smaller than the predetermined P-V amplitude, and the transverse balance adjustment is completed in step ST60, the adjustment of the movable base 51 of the rotary machine 50 is completed.

An amplitude of a rotary machine 50 that has been subjected to the balance adjustment using the adjustment method of the adjustment device 1 of the embodiment described above is shown in FIG. 12. It should be noted that the amplitude waveform of FIG. 12 is obtained by further adjustment, by using the adjustment device 1 of the present invention, the rotary machine 50 shown in FIG. 15 the amplitude of which has been reduced by using the conventional influence coefficient method.

Figure 16:
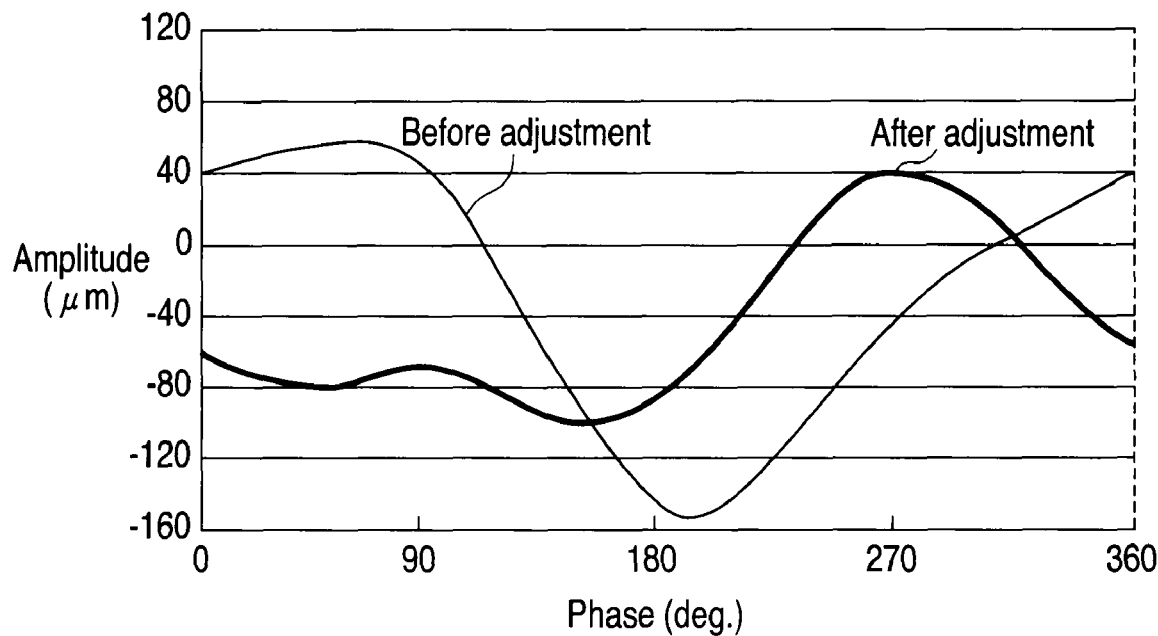
FIG. 16 is an explanatory view showing an example of an amplitude waveform at the time of adjustment of the conventional rotary machine.
Figure 17:
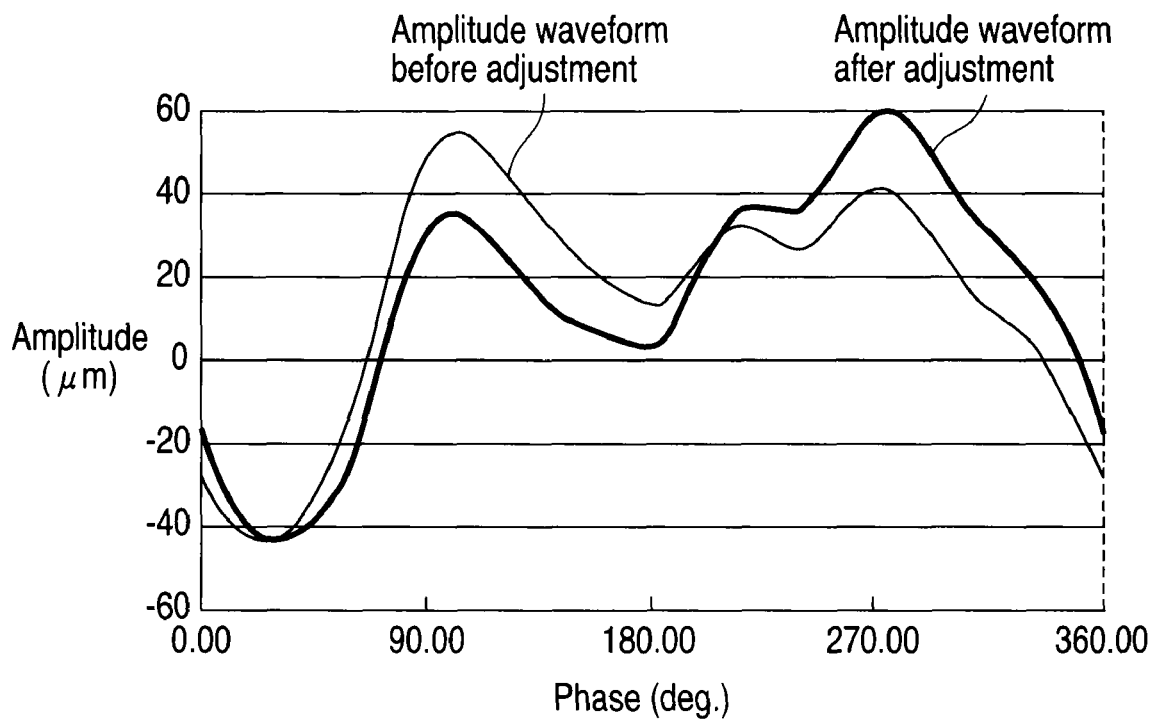
FIG. 17 is an explanatory view showing an example of an amplitude waveform at the time of adjustment of the conventional rotary machine.

As shown in FIG. 16, the P-V amplitude of a rotary machine 50 which has not been adjusted after the manufacture is about 200 μm, and when the amplitude is reduced by using the conventional influence coefficient method, the P-V amplitude becomes 140 μm. Further, when the rotary machine 50 the amplitude of which has been reduced by using the conventional influence coefficient method is adjusted by using the adjustment device 1, it becomes possible to reduce the P-V amplitude up to 54 μm. That is, according to the adjustment method of this embodiment, it becomes possible to reduce the amplitude more than the conventional influence coefficient method.

According to the rotary machine 50 and the adjustment device 1 of the rotary machine configured as described above, a waveform of an amplitude of the transverse vibration produced at the time of rotation of the rotary machine 50 is approximately expressed on the basis of a function by the PC 20, and the optimum weight and position (angle) of the adjustment weight 30 are calculated. The calculated optimum adjustment weight 30 is arranged on the movable base 51. Likewise, the optimum weight, movement amount, and position (angle) of the adjustment weight 30 are calculated from an amplitude of the longitudinal vibration, and the optimum adjustment weight 30 is arranged on the movable base 51.

As a result of this, all that is needed is to arrange the adjustment weight 30 on the movable base in accordance with the change amount and position (angle) of the adjustment weight 30 displayed on the display section 23 of the PC 20. This makes the adjustment of the rotary machine 50 easy. Further, as for the arrangement of the adjustment weight 30, it is only required to increase/decrease or move the adjustment weight 30 within the storage section 60 provided on the movable base 51. Accordingly, the adjustment becomes easier, and the workability is also improved.

Further, as for attachment/detachment of the adjustment weight 30, the optimum adjustment weight 30 is calculated by the adjustment device such as the PC 20, and the like, and hence the number of times thereof may be several times (about one to two times). That is, the number of times of the attachment/detachment of the adjustment weight 30 is small, the workability is improved, and the adjustment steps are reduced. As a result of this, it becomes possible to reduce the adjustment time, and reduce the adjustment cost. Further, by repeating the steps of calculating the optimum adjustment weight 30 by means of the adjustment device 1, and arranging the optimum adjustment weight 30, it becomes also possible to make the balance adjustment highly accurate.

Further, it becomes possible to use the influence wave functions $f_A(x, \theta_A)$ and $f_B(y', \theta_B)$ of the vibration data $A_0$ and $B_0$ calculated in steps ST11 to ST14, and steps ST51 to ST54 by the vibration adjustment of the rotary machine 50 also for another rotary machine 50 of the same shape. That is, in another rotary machine 50 of the same shape, each part is substantially identical except for the variation resulting from the dimensional accuracy, and hence the calculation step of the influence wave function can be omitted.

By using the same influence wave function as described above, it becomes possible to reduce the adjustment step, reduce the adjustment step at the time of mass production, improve the productivity, and reduce the adjustment cost.

Further, even when the rotary machine 50 is rotated, the amplitude waveform is approximately calculated from the influence wave function as a factor other than the balance, and the adjustment weight 30 is obtained so that the amplitude waveform can be reduced. The movement and increase/decrease are targeted for the obtained adjustment weight 30. This reduces the vibration. As a result of this, it becomes possible to effectively reduce the vibration even with respect to an increase in the amplitude caused when the rotary machine 50 is operated at a high rotational speed. Further, by using a rotary machine 50 the vibration of which is reduced in an X-ray CT apparatus, it becomes possible to reduce the shake of the tomographic image resulting from the vibration, and output an image of high image quality.

Further, regarding the vibration adjustment, by adjusting the transverse and longitudinal vibration of the rotary machine 50, it becomes possible to reduce the transverse and longitudinal vibration of the rotary machine 50. As the order of the vibration adjustment, after the adjustment of the transverse vibration, the longitudinal vibration is adjusted, whereby the movement of the adjustment weight 30 in the latter adjustment is to be axial, and hence the vibration reduced by the former transverse vibration adjustment is never increased.

As described above, according to the adjustment device 1 and the adjustment method of the rotary machine 50 associated with this embodiment, it becomes possible to improve the adjustment accuracy, and effectively reduce the vibration. Further, it becomes also possible to improve the workability, and the productivity. As a result of this, it becomes also possible to reduce the manufacturing cost.

It should be noted that modification examples other than the embodiment of the invention described above will be described below. For example, in the example described above, it has been described that the rotary machine 50 is used for the X-ray CT apparatus. However, this is not limited to the X-ray CT apparatus. For example, the above embodiment may be applied to a wheel or a steering gear. That is, any rotating body that produces vibration by rotation can be reduced in vibration irrespectively of the size and shape thereof.

Further, in the example described above, it has been described that the PC 20 is used as the vibration measuring instrument and the calculation means. However, this is not limited to the PC 20. For example, the configuration may be such that the vibration sensor 10 is connected to a vibration measuring instrument such as a waveform output device with an amplifier through the signal line S, and a PC and other calculation device are connected to the vibration measuring instrument. Even when a device in which the vibration sensor 10 and the vibration measuring instrument are integrated with each other is used, the present invention can be applied thereto.

Further, in the example described above, the configuration is such that when one vertex of the movable base 51 is assumed to be at a 0° position, two storage sections 60 separate from each other by a predetermined distance t are provided at three positions of 120°, 180°, and 240°. However, the positional relationships between the storage sections 60 are not limited to the above. For example, the storage sections 60 may be provided at intervals of 60° from 0 to 360°, or may be provided at two or more positions in the thickness direction of the movable base. That is, the present invention can be applied when the adjustment weight 30 can be moved and increased/decreased at each position.

Further, the configuration in which in step ST16 described above, the change amount x and the position $\theta_A$ that minimize the P-V amplitude are obtained by the PC 20, and in steps ST34 (YES) and ST35, comparison between $S_S$ and $S_{min}$ is performed by the PC 20, and each value is replaced has been described. However, the configuration is not limited to this. For example, a configuration in which the comparison between the P-V amplitudes in step ST34 is not performed by the PC 20, and a list of influence wave data and the like obtained from the approximate expression is displayed on the display section, and the operator who performs adjustment makes a judgment may be employed.

It should be noted that the present invention is not limited to the above-mentioned embodiment as it is, and the constituent elements may be modified and embodied in the implementation stage within the scope not deviating from the gist of the invention. Further, by appropriately combining a plurality of constituent elements disclosed in the above embodiment with each other, various inventions can be formed. For example, some constituent elements may be deleted from the entire constituent elements shown in the embodiment. Further, constituent elements of different embodiments may be appropriately combined with each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A device comprising:
   a rotary machine including a movable base, the movable base formed in an annular shape and configured to rotate around an axis so as to enable an object to move inside the annular shape;
   a vibration measuring instrument configured to, when the movable base is rotated, measure an amplitude of vibration of the rotary machine along each of the axis and a direction orthogonal to the axis; and
   means for calculating a position and a weight of an adjustment weight to be provided on the movable base based on the amplitude of vibration measured by the vibration measuring instrument, so that the weight of the adjustment weight can be adjusted, and the adjustment weight can be moved along the axis, wherein the position and the weight of the adjustment weight minimize the amplitude of vibration of the movable base;
   wherein the means for calculating comprises:
      means for obtaining first influence wave data from a difference between first adjustment amplitude data corresponding to a rotational angular position of the movable base measured orthogonally by the vibration measuring instrument when the adjustment weight having an arbitrary weight is arranged at an arbitrary circumferential position of the movable base, and the movable base including the adjustment weight is rotated, and second adjustment amplitude data corresponding to a rotational angular position of the movable base measured orthogonally by the vibration measuring instrument when the adjustment weight is changed by moving the adjustment weight circumferentially relative to the movable base or by increasing/decreasing the adjustment weight, and the movable base is rotated;
      means for obtaining an approximate expression of the first influence wave data based on the influence wave data and a change in the adjustment weight; and
      means for calculating first approximate influence wave data of the conditions of the adjustment weight by substituting a plurality of conditions of an arbitrary position and weight of the adjustment weight into the approximate expression.

2. The adjustment device of a rotary machine according to claim 1, wherein
   the means for obtaining first influence wave data calculates second influence wave data from a difference between third adjustment amplitude data corresponding to a rotational angular position of the movable base measured along the axis by the vibration measuring instrument axis when the adjustment weight having an arbitrary weight is arranged at an arbitrary circumferential position of the movable base, and the movable base including the adjustment weight is rotated, and fourth adjustment amplitude data corresponding to a rotational angular position of the movable base measured along the axis by the vibration measuring instrument when the adjustment weight is moved along the axis of the movable base, and the movable base is rotated,
   the-means for obtaining the approximate expression derives an approximate expression of the second influence wave data based on the second influence wave data and a change amount resulting from the movement of the adjustment weight, and
   the means for calculating calculates second approximate influence wave data from the change amount of the adjustment weight by using the approximate expression of the second influence wave data.

3. An adjustment method comprising:
   measuring, in a rotary machine including a movable base formed in an annular shape and configured to rotate around an axis so as to enable an object to move inside the annular shape, an amplitude of vibration of the rotary machine along the axis and a direction orthogonal to the axis when the movable base is rotated;
   calculating a position and a weight of an adjustment weight by using calculation means, based on the measured amplitude of vibration so that the amplitude of vibration of the movable base is minimized; and
   adjusting the adjustment weight on the movable base based on the position and the weight of the adjustment weight calculated by the calculation means;
   wherein the calculating step comprises:
      obtaining first influence wave data by calculating a difference between first adjustment amplitude data corresponding to a rotational angular position of the movable base at a time the adjustment weight having an arbitrary weight is arranged at an arbitrary circumferential position of the movable base, and the movable base including the adjustment weight is rotated, and second adjustment amplitude data corresponding to a rotational angular position of the movable base measured orthogonally when the adjustment weight is changed by moving the adjustment weight circumferentially relative to the movable base or by increasing/decreasing the adjustment weight, and the movable base is rotated;
      deriving an approximate expression of the first influence wave data based on the influence wave data and a change in the adjustment weight; and
      calculating first approximate influence wave data of the conditions of the adjustment weight by substituting a plurality of conditions of an arbitrary position and weight of the adjustment weight into the approximate expression.

4. The adjustment method of a rotary machine according to claim 3, wherein the calculating step further comprises:
   obtaining second influence wave data by calculating a difference between third adjustment amplitude data corresponding to a rotational angular position of the movable base at the time the adjustment weight having an arbitrary weight is arranged at an arbitrary circumferential position of the movable base, and the movable base including the adjustment weight is rotated, and fourth adjustment amplitude data corresponding to a rotational angular position of the movable base at the time the adjustment weight is moved along the axis of the movable base, and the movable base is rotated, deriving an approximate expression of the second influence wave data based on the second influence wave data and a change amount resulting from the movement of the adjustment weight, and calculating second approximate influence wave data from the change amount of the adjustment weight by using the approximate expression of the second influence wave data.

5. A manufacturing method of a rotary machine, comprising:

assembling a rotary machine including a rotatable movable base and a stationary base for supporting the movable base;

measuring an amplitude of vibration of the rotary machine along an axis and a direction orthogonal to the axis when the movable base is rotated;

calculating a position and a weight of an adjustment weight by using calculation means based on the measured amplitude of vibration so that the amplitude of vibration of the movable base is minimized, wherein the calculating step further comprises obtaining first influence wave data by calculating a difference between first adjustment amplitude data corresponding to a rotational angular position of the movable base at a time the adjustment weight having an arbitrary weight is arranged at an arbitrary circumferential position of the movable base, and the movable base including the adjustment weight is rotated, and second adjustment amplitude data corresponding to a rotational angular position of the movable base measured orthogonally when the adjustment weight is changed by moving the adjustment weight circumferentially relative to the movable base or by increasing/decreasing the adjustment weight, and the movable base is rotated;

deriving an approximate expression of the first influence wave data based on the influence wave data and a change in the adjustment weight; and calculating first approximate influence wave data of the conditions of the adjustment weight by substituting a plurality of conditions of an arbitrary position and weight of the adjustment weight into the approximate expression; and attaching the adjustment weight to the movable base based on the position and the weight of the adjustment weight calculated by the calculation means.

6. The manufacturing method of a rotary machine according to claim 5, wherein the calculating step further comprises:

obtaining second influence wave data by calculating a difference between third adjustment amplitude data corresponding to a rotational angular position of the movable base at the time the adjustment weight having an arbitrary weight is arranged at an arbitrary circumferential position of the movable base, and the movable base including the adjustment weight is rotated, and fourth adjustment amplitude data corresponding to a rotational angular position of the movable base at the time the adjustment weight is moved along the axis of the movable base, and the movable base is rotated;

deriving an approximate expression of the second influence wave data based on the second influence wave data and a change amount resulting from the movement of the adjustment weight; and calculating second approximate influence wave data from the change amount of the adjustment weight by using the approximate expression of the second influence wave data.

7. The manufacturing method of a rotary machine according to claim 5, wherein the rotary machine is an X-ray CT apparatus; and
the movable base includes an X-ray tube and a detector.

* * * * *